US011026830B2

(12) United States Patent
Wortelboer et al.

(10) Patent No.: US 11,026,830 B2
(45) Date of Patent: Jun. 8, 2021

(54) TONGUE ADVANCER SYSTEM FOR USE IN A TONGUE MANIPULATION SYSTEM

(71) Applicant: KONINKLIJKE PHILIPS N.V., Eindhoven (NL)

(72) Inventors: Pippinus Maarten Robertus Wortelboer, Eindhoven (NL); Michel Paul Barbara Van Bruggen, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 904 days.

(21) Appl. No.: 15/534,726

(22) PCT Filed: Nov. 27, 2015

(86) PCT No.: PCT/EP2015/077857
§ 371 (c)(1),
(2) Date: Jun. 9, 2017

(87) PCT Pub. No.: WO2016/091611
PCT Pub. Date: Jun. 16, 2016

(65) Prior Publication Data
US 2017/0319377 A1    Nov. 9, 2017

(30) Foreign Application Priority Data
Dec. 12, 2014  (EP) ..................................... 14197694

(51) Int. Cl.
*A61F 5/56*         (2006.01)
(52) U.S. Cl.
CPC ................... *A61F 5/566* (2013.01)

(58) Field of Classification Search
CPC ...... A61B 17/0401; A61B 17/00; A61B 17/04; A61B 17/08; A61F 5/58; A61F 5/56; A61F 5/14; A61F 5/566; A61F 2005/563; A61F 2/20; A61F 2/00; A61F 5/08; A61M 5/00; A61M 2005/14252; A61C 8/0093; A61C 5/90; A61C 7/08
USPC .......... 128/860, 848, 859, 861, 862; 606/60, 606/191, 232; 604/104; 602/232
See application file for complete search history.

(56) References Cited

U.S. PATENT DOCUMENTS 9,504,829 B2 *   11/2016  Spinelli ................ A61N 1/0551
10,512,480 B2 *  12/2019  Beeby ................. A61B 17/3468
2005/0092332 A1 *  5/2005  Conrad .................... A61F 5/566
                                                                   128/898
2006/0020247 A1   1/2006  Kagan et al.
(Continued)

FOREIGN PATENT DOCUMENTS

WO    2007149469 A2    12/2007
WO    2013118069 A2    8/2013

*Primary Examiner* — Ophelia A Hawthorne (57) ABSTRACT

A tongue advancer system is for use in a tongue manipulation device, comprising a tissue anchor having a set of retractable fingers having a retracted configuration in which the tissue anchor is adapted to be loaded into a delivery tube and a deployed configuration in which the fingers are adapted for extending into tongue tissue in forward and lateral directions. The system further comprises a spacer which extends beyond the maximum forward extent of the retractable fingers. The spacer ensures that the fingers do not puncture the tongue surface.

14 Claims, 7 Drawing Sheets

(56) References Cited

U.S. PATENT DOCUMENTS

| | | | |
|---|---|---|---|
| 2007/0106330 A1* | 5/2007 | Rosenberg | A61M 25/04 |
| | | | 606/232 |
| 2008/0023012 A1 | 1/2008 | Dineen et al. | |
| 2008/0035160 A1* | 2/2008 | Woodson | A61F 5/566 |
| | | | 128/860 |
| 2009/0287229 A1 | 11/2009 | Ogdahl | |
| 2010/0108077 A1 | 5/2010 | Lindh et al. | |
| 2010/0256679 A1 | 10/2010 | Ducharme | |
| 2011/0144421 A1 | 6/2011 | Gillis et al. | |
| 2013/0186412 A1 | 7/2013 | Weadock et al. | |
| 2013/0233324 A1 | 9/2013 | Witt et al. | |
| 2015/0064651 A1 | 3/2015 | Zhang et al. | |

\* cited by examiner

TONGUE ADVANCER SYSTEM FOR USE IN A TONGUE MANIPULATION SYSTEM

CROSS-REFERENCE TO PRIOR APPLICATIONS

This application is the U.S. National Phase application under 35 U.S.C. § 371 of International Application Serial No. PCT/EP2015/077857, filed on 27 Nov. 2015, which claims the benefit of European Application No. 14197694.4, filed on 12 Dec. 2014. These applications are hereby incorporated by reference herein.

FIELD OF THE INVENTION

This invention relates to a tongue advancer system for use in a tongue manipulation system.

BACKGROUND OF THE INVENTION

It is known to use a tongue manipulation device to treat upper airway obstruction and sleep disordered breathing.

Respiratory disorders during sleep are recognized as a common problem with significant clinical consequences. Obstructive Sleep Apnoea (OSA) causes an intermittent cessation of airflow. When these obstructive episodes occur, an affected person will transiently arouse. Because these arousal episodes typically occur 10 to 60 times per night, sleep fragmentation occurs which produces excessive daytime sleepiness. Some patients with OSA experience over 100 transient arousal episodes per hour. OSA may also lead to cardiovascular and pulmonary disease.

Various approaches are known which aim to maintain the airway passage during sleep. Oral appliances aimed at changing the position of the soft palate, jaw or tongue are available, but patient discomfort has limited their use. Continuous Positive Airway Pressure (CPAP) devices are often used as first-line treatments for OSA. These devices use a sealed mask which produces airflow at a slightly elevated pressure and acts to maintain positive air pressure within the airway.

This disclosure relates to an approach by which a tongue manipulation device can be surgically applied to a patient. The complete device comprises three essential parts:

(i) a tissue anchor which is surgically placed inside the tongue (this is also sometimes called the tongue advancer);

(ii) a bone anchor which is typically attached to the mandible; and (iii) a tether line which fixes the tissue anchor to the bone anchor.

The bone anchor may feature a spool, enabling the surgeon to spool the tether into the bone anchor. This process is called adjustment and stabilizes the tongue as well as advances the tongue in the direction of the mandible (or prevents the tongue moving back), preventing blocking of the airway.

Generally, the implant is placed in the midline of the tongue at the base of the tongue and the device provides stabilization and advancement of the tongue base, so that the tongue can no longer move freely back. Instead, it is blocked by the tether line(s) connecting the bone anchor and tissue anchor.

The tissue anchor may be formed from a shape memory material such as Nitinol. The tissue anchor is loaded into a long but relatively small delivery tube that can be brought into the tongue. The tissue anchor is deployed into the tongue base when pushed out of this small delivery tube further. This causes a set of fingers (or barbs) to extend into the tongue tissue. The tissue anchor provides a stable hooking in the weak tongue tissue and, with the tether attached to the proximal side, the tongue base can be advanced to keep the airway open.

The tether is then locked in the advance position in some way. By using a tissue anchor that is deployable from a delivery tube, delivery into the tongue can be through a relatively small diameter tube, and the tissue anchor can also be removed through a similar tube.

The delivery channel in the tongue in which the delivery tube sits is created by a solid trocar with a sharp tip inside a cannula. The depth of insertion is controlled manually by pushing in the trocar with one hand and palpating the tongue surface in the mouth with the other.

The trocar is then withdrawn leaving the cannula in place, which defines a channel for delivery of the tissue anchor. A tissue anchor delivery tube is connected to the cannula before deployment. This ensures the tissue anchor is delivered to a known location with respect to the cannula. The cannula essentially becomes the last section of the delivery tube.

The cannula is not fixed in the subject. It may happen that in the course of the implantation procedure the cannula moves deeper into the tongue. It is difficult to palpate the position at the tongue surface, since the sharp tip of the trocar which provided position feedback is no longer present. If the delivery tool loaded with the tissue anchor is pushed slightly too far into the tongue, the fingers of the tissue anchor may penetrate the tongue surface.

There is therefore a need for a tissue anchor design which can avoid tongue puncturing resulting from unintended posterior displacement of the cannula.

SUMMARY OF THE INVENTION

The invention is defined by the claims.

Examples in accordance with an aspect of the invention provide an implantable tongue advancer system for use in a tongue manipulation device, comprising:

a tissue anchor comprising a set of retractable fingers having a retracted configuration in which the tissue anchor is adapted to be loaded into a delivery tube and a deployed configuration in which the fingers are adapted for extending into tongue tissue in forward and lateral directions; and a spacer which extends beyond the maximum forward extent of the retractable fingers.

The spacer is a part of a tongue advancer system, but it is for example a separate component to the tissue anchor, and it may in practice be applied to the tissue anchor or it may be applied to the delivery equipment. In this text, the component which has fingers which grip the tongue tissue is named a "tissue anchor" and the overall system which is implanted is named a "tongue advancer system" or "implantable tongue advancer system" i.e. including the spacer which is the subject of this invention. The "tissue anchor" is also referred to in the literature as the "tongue anchor" or the "tongue advancer".

The spacer may for example be added to the tissue anchor when it is loaded into a delivery tube or it may be applied to the delivery tube itself.

This spacer preferably has a blunt head which can push the tongue tissue in front without a risk of cutting deeper into the channel previously made by a trocar. The way the spacer projects beyond the fingers means that the deploying fingers stay away from the (possibly lifted) tongue surface, thus reducing the risk that any finger punctures the tongue surface.

The amount by which the spacer extends can be optimized; it should be long enough to avoid tongue puncturing at deployment and it should not create unnecessary tongue surface lifting or subcutaneous volume increase if the spacer is to remain implanted in the tongue.

In a first set of examples, in the retracted configuration, the fingers are straight and extend in an axial direction, (which direction is the same as the direction of insertion into the tongue and also corresponds to the direction of the elongate axis of the delivery tube), wherein in a plane perpendicular to the axial direction, the fingers are arranged in a ring. The spacer comprises a shaft inside the ring. This means the spacer can simply be pushed down the centre of the retracted tissue anchor, and it can have the form of a rod with a solid flat and therefore blunt end to push against tongue tissue.

The shaft may extend from a back end of the fingers to a location which projects beyond the forward end of the fingers (i.e. the tips of the fingers) when the fingers are in their refracted configuration. This forward projection prevents the fingers penetrating the distal tongue surface.

The fingers in the deployed configuration may have a loop radius, and the shaft projects beyond the forward end (in the retracted configuration) by an amount corresponding to the loop radius.

The shaft may be compressible in the axial direction. As the tissue anchor is pushed forward to deploy the fingers, the shaft does not need to advance by a corresponding amount—it just needs to maintain clearance between the most advanced part of the deploying fingers and the end of the shaft.

The shaft may comprise a cylinder with slits along its length. These slits then define an annular set of double-clamped beams, which can expand outwardly to implement the compressing. These double-clamped beams can be considered to function as plate springs. The double-clamped beams may have an initial outward deformation so that they will deform outwardly when compressed. Alternatively, the shaft may be formed of an elastic material.

The shaft may alternatively comprise a base and a head with a non-rigid interconnection between the base and the head. This non-rigid connection allows bending to implement compression (where compression means a reduction in the overall dimension in the axial direction corresponding to the elongate axis of the delivery tube).

In another set of examples, in the retracted configuration, the fingers are straight and extend in an axial direction, wherein the spacer comprises an annular ring around the ends (i.e. the tips) of the fingers in the retracted configuration. By providing a ring around the ends, it projects beyond those ends. The fingers are then configured to extend through the annular ring in the extended configuration. This ring can be added as an extension piece to a delivery tube, and it is preferably of a soft material which can be pierced by the fingers.

In another set of examples, in the retracted configuration, the fingers are straight and extend in an axial direction, wherein the spacer comprises a cap over the ends (i.e. the tips) of the fingers in the refracted configuration. This cap functions in the same way as the annular ring, and again the fingers preferably extend through the cap in the extended configuration.

In all examples, the spacer may be biodegradable so that it is left in the tongue and then degrades over time.

The invention also provides a tongue manipulation system, comprising a tongue advancer system as defined above, and a bone anchor for attachment to the mandible. A tether line is then preferably provided which couples the tissue anchor of the tongue advancer system to the bone anchor.

The invention also provides a tissue anchor comprising:
a set of retractable fingers having a retracted configuration in which the tissue anchor is adapted to be loaded into a delivery tube and a deployed configuration in which the fingers are adapted for extending into tongue tissue in forward and lateral directions; and
a loading space between the fingers adapted to receive a spacer for extending beyond the maximum forward extent of the retractable fingers.

An audible or tactile feedback arrangement may be provided in the loading space to give a user an indication of when the spacer is correctly inserted into the loading space.

The invention also provides a delivery tube for use in applying a tongue advancer system into the tongue, the tongue advancer system comprising a tissue anchor having a set of retractable fingers having a retracted configuration in which the tissue anchor is adapted to be loaded into the delivery tube and a deployed configuration in which the fingers are adapted for extending into tongue tissue in forward and lateral directions, wherein the delivery tube comprises a first section for insertion and removal from the tongue tissue and a second section at the remote end which: i) functions as a spacer which extends beyond the maximum forward extent of the retractable fingers, wherein the fingers are adapted to be able to pierce the spacer, or ii) is adapted to receive a spacer (70, 80) which extends beyond the maximum forward extent of the retractable fingers.

This piercing of the spacer takes place when the fingers of the tissue anchor are deployed.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a tongue advancer system for use in a tongue manipulation device, comprising a tissue anchor having a set of retractable fingers having a retracted configuration in which the tissue anchor is adapted to be loaded into a delivery tube and a deployed configuration in which the fingers are adapted for extending into tongue tissue in forward and lateral directions. The system further comprises a spacer which extends beyond the maximum forward extent of the retractable fingers ("forward" being the axial insertion direction of the tissue anchor into the tongue from the delivery tube). The spacer ensures that the fingers do not puncture the tongue surface.

The invention relates to the tissue anchor part of a tongue manipulation device. The tissue anchor is for attachment to the tongue, and the device further comprises a bone anchor typically for attachment to the mandible and a tether line which fixes the tissue anchor to the bone anchor.

The invention can be applied as a modification to known devices, for example of the type described in detail in US 2008/0023012, which is hereby incorporated by reference.

The general overall operation of the known device will first be described, with reference to FIGS. 1 to 3 which are adapted from US 2008/0023012.

Figure 1:
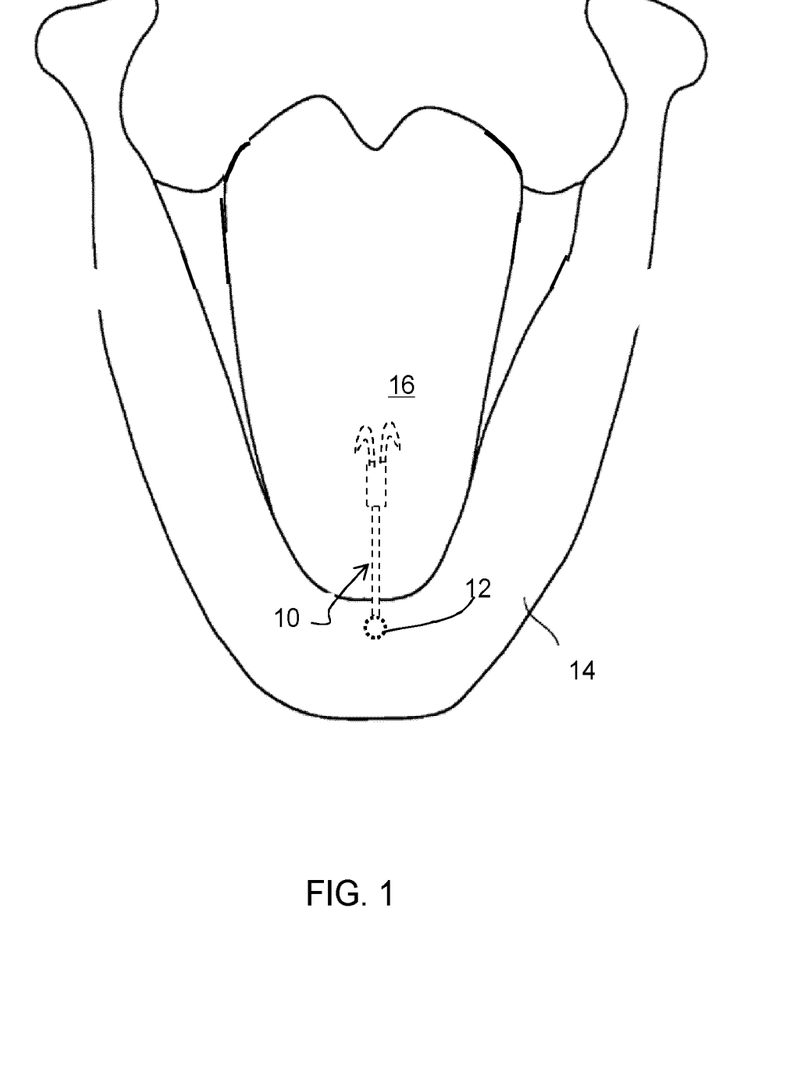
FIG. 1 shows generally how a known tongue manipulation device is used.

FIG. 1 shows a tongue manipulation device 10 attached to a securing assembly 12 located on the inferior surface of the mandible 14. The tongue is shown as 16.

Figure 2:
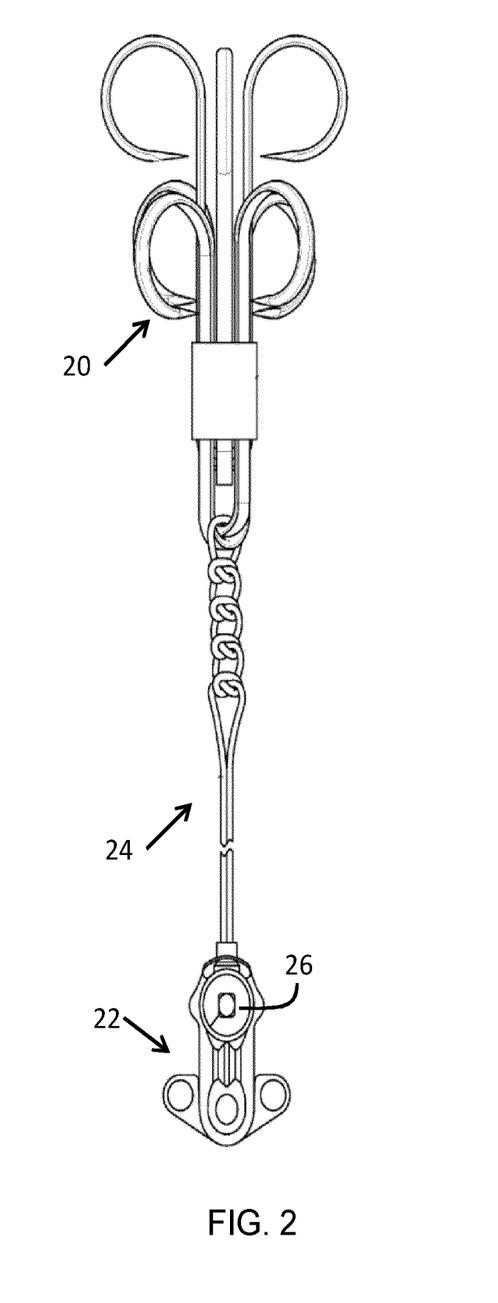
FIG. 2 shows the known tongue manipulation device in more detail.

FIG. 2 shows a possible design of the tongue manipulation device in more detail.

It comprises a tongue advancer in the form of a tissue anchor 20 for attachment (in particular implantation) to the tongue and a bone anchor 22 for attachment to the mandible. A tether line 24 fixes the tissue anchor 20 to the bone anchor.

The bone anchor 22 comprises a tether line spool arrangement 26. This enables the tether line to be wound onto the spool to take up slack in the tether line so that the line can provide a desired restricted movement of the tongue.

Figure 3:
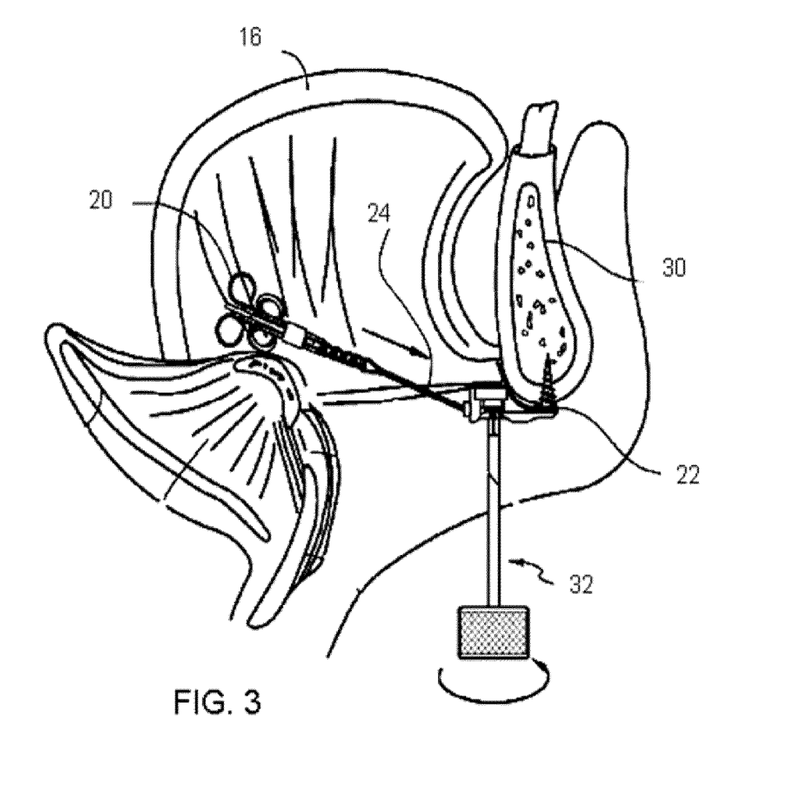
FIG. 3 shows how the tension in the tether line is adjusted in the device of FIGS. 1 and 2.

FIG. 3 shows how adjustment of the spool is made, and shows a cross section through the lower part of the head of a patient. The bone anchor 22 is attached to the lower mandible 30 as shown. To tighten the tether line 24, a rotary drive shaft 32 (known as a "titration needle" or "adjustment tool") is inserted into an opening in the spool part of the bone anchor, and adjustment is judged based on an indexed function.

The invention provides designs of tongue advancer system which make use of a spacer to prevent tongue piercing. There are three different conceptual approaches. FIGS. 4 to 7 relate to a first conceptual approach which provides a spacer as an extension piece to the tissue anchor.

Figure 4:
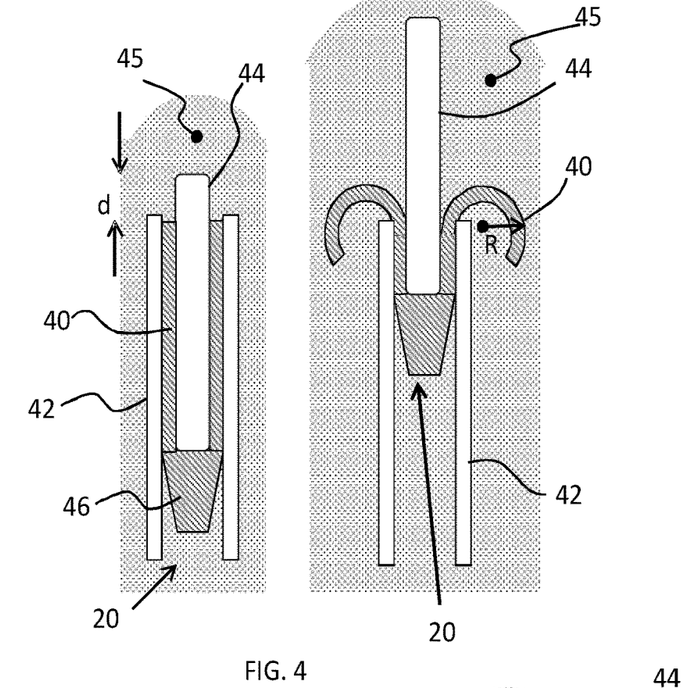
FIG. 4 shows a first example of tongue advancer system.

FIG. 4 shows a first example of tongue advancer system with tongue puncture protection.

The tissue anchor 20 is essentially as described above. There is a set of retractable fingers 40 having a refracted configuration (left image) in which the tissue anchor is adapted to be loaded into a delivery tube 42, and a deployed configuration (right image) in which the fingers are adapted for extending into tongue tissue in forward and lateral directions with respect to the delivery tube 42.

The tongue advance system has a spacer 44 which extends beyond the maximum forward extent of the retractable fingers 40. In this example it has the form of a shaft or rod. This maximum forward extent is the maximum distance the fingers 40 project beyond the end of the delivery tube 42 during deployment of the tissue anchor. The fingers roll into curved arcs when deployed from the end the delivery tube 42, and these arcs extend forwardly from the end of the delivery tube as well as laterally into the tongue tissue. Where they extend forwardly, they penetrate deeper into the tongue tissue than the end of the delivery tube 42, which sits in the channel made by the trocar. This forward penetration risks puncturing the tongue, although lateral penetration can also be a risk if the tongue surface is not flat.

The spacer 44 can be added to the tissue anchor 20 when it is loaded into the delivery tube. The spacer 44 has a blunt head which can push the tongue tissue in front away without a risk of cutting deeper into the channel previously made by a trocar.

FIG. 4 shows how the fingers form a radius of curvature of R, and the distance d by which the spacer projects from the ends of the refracted fingers may be at least as large as this radius. The projection means that the deploying fingers stay away from the tongue surface, thus reducing the risk that any finger punctures the tongue surface. The tongue volume is shown as region 45.

The fingers 40 may in the retracted configuration be straight and arranged in a ring so that there is a hollow center. The spacer shaft can be housed inside the ring. It can only be inserted until it reaches a head 46 of the tissue anchor component. Thus, the shaft extends from a back end of the fingers to a location which projects beyond the forward end of the fingers when the fingers are in their retracted configuration.

The version of FIG. 4 essentially provides an extension to the tissue anchor.

The shaft 44 may be of biodegradable material.

Figure 5:
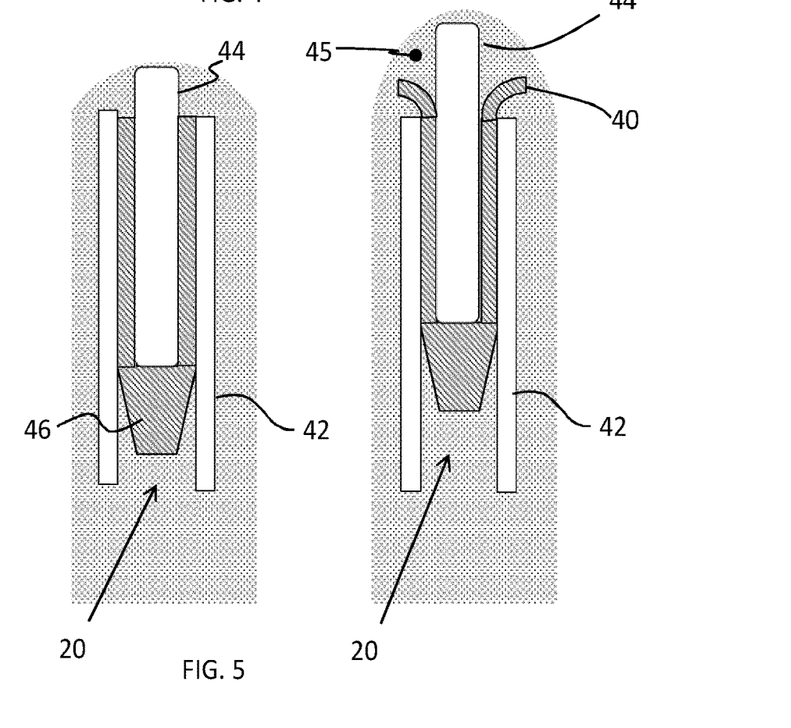
FIG. 5 is used to explain why a certain degree of extension is desirable in used of the system of FIG. 4.

In use, the physician inserts the tongue advancer system into the channel in the tongue defined by the delivery tube 42 until he feels the tip of the shaft 44 beneath the tongue surface inside the mouth. For an extension distance in the retracted configuration equal to the loop radius, the surface of the tongue just before deployment should be almost flat. Otherwise the fingers might still stick through the surface as the circular deployment path of the fingers moves the sharp finger tips outwards. This is illustrated in FIG. 5. The right image in FIG. 5 shows the fingers on the verge of piercing the surface of the tongue 45 during deployment. A larger initial extension distance d can provide a safety factor.

A further option to reduce the puncture risk is to use a deformable spacer that compresses in length (and correspondingly extends in width) when it experiences a compression force.

Figure 6:
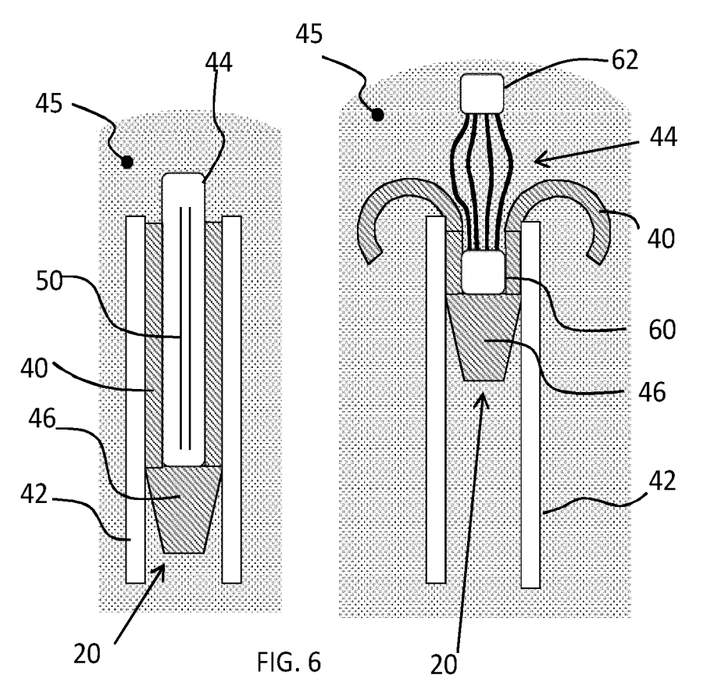
FIG. 6 shows a second example of tongue advancer system.

FIG. 6 shows a second example which makes use of a compressible spacer. The spacer again comprises a shaft 44, but it has axial slits 50 along its length direction so that a set of double-clamped beams is defined. These beams connect a lower part 60 and an upper part 62 of the shaft 44. In the unloaded state, these beams have a slightly curved shape with the middle section farther away from the centreline. Under a compressive load, the beams can buckle outwards thus creating a larger diameter of the spacer and a shorter length. This is shown for the deployed configuration in the right image. The double-clamped beams need to be sufficiently thin or sharp to create the space in radial direction themselves; there is no cavity made previously by the trocar at these radially outward locations.

The spacer structure can be preloaded, so that the spacer is held in its extended shape when housed in the delivery tube, but the spacer then tends to recover its initial wide shape without the need for such a large axial compression force. A wider initial shape will reduce the required compression force, but this will require a larger inward preloading force when loading the tissue anchor into the delivery tube.

The same concept of making use of a wider spacer that is compressed in width and extended in length into the available space of the delivery tube can also be achieved using an elastic spacer material. In this case, the spacer may not need the slit structure.

The bottom 60 of the spacer remains in place in the bottom of the cavity between the fingers 40 even after deployment.

Figure 7:
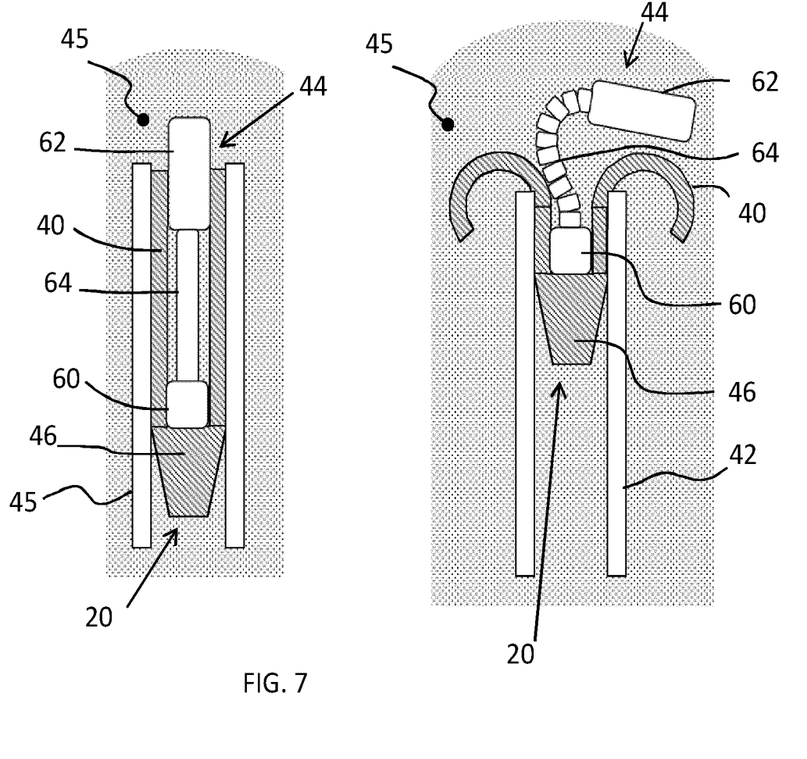
FIG. 7 shows a third example of tongue advancer system.

FIG. 7 shows a third example in which the shaft comprises a base 60 and a head 62 with a non-rigid interconnection 64 between the base and the head.

The blunt top part 62 of the spacer is clamped within the cavity formed by the fingers when the tissue anchor is in the retracted configuration (left image). After partial deployment, the top part is disconnected from the fingers and only remains connected with the lower part 60 of the spacer via the flexible part 64, for example a thinner connecting member. As a result, the top part 62 can bend out and find a place below the tongue surface without pushing it unnecessarily far up. The spacer can be of different materials and the thinner part can also be connected to the tissue anchor by means of screwing or knotting.

The designs described above each allow recapturing of the spacer if the tissue anchor is to be withdrawn from the tongue. This withdrawal is a known feature in the existing system as long as the tissue anchor is not yet disconnected from the delivery tube. This feature allows repositioning of the tissue anchor if desired. Thus, these examples also enable the tissue anchor and the spacer to be retracted back into a delivery tube in simple manner. The dimensions can be optimized depending on the tongue tissue and surface properties.

In the examples of FIGS. 4 to 7, before using the tongue advancer system, the spacer 44 is loaded into the space between the fingers 40. There can be an indication given when the spacer has reached the desired depth, for example the spacer may be a snapfit into the space between the fingers (which will give at least audible feedback), or there may be other tactile or audible feedback provided when the spacer is fully inserted. Another option to hold the spacer in the space between the fingers 40 uses screw thread. Other options will be evident to a skilled person Thus, in these examples, there is provided a tissue anchor (20) comprising a set of retractable fingers (40) having a retracted configuration in which the tissue anchor is adapted to be loaded into a delivery tube (42) and a deployed configuration in which the fingers are adapted for extending into tongue tissue (45) in forward and lateral directions, and the space between the fingers is a loading space for receiving a spacer (44) for extending beyond the maximum forward extent of the retractable fingers. An audible or tactile feedback arrangement is for example provided in the loading space. Tactile feedback may be given when the spacer is fully inserted because it reaches a stop, or there may be a snap-fit sound and feel.

Figure 8:
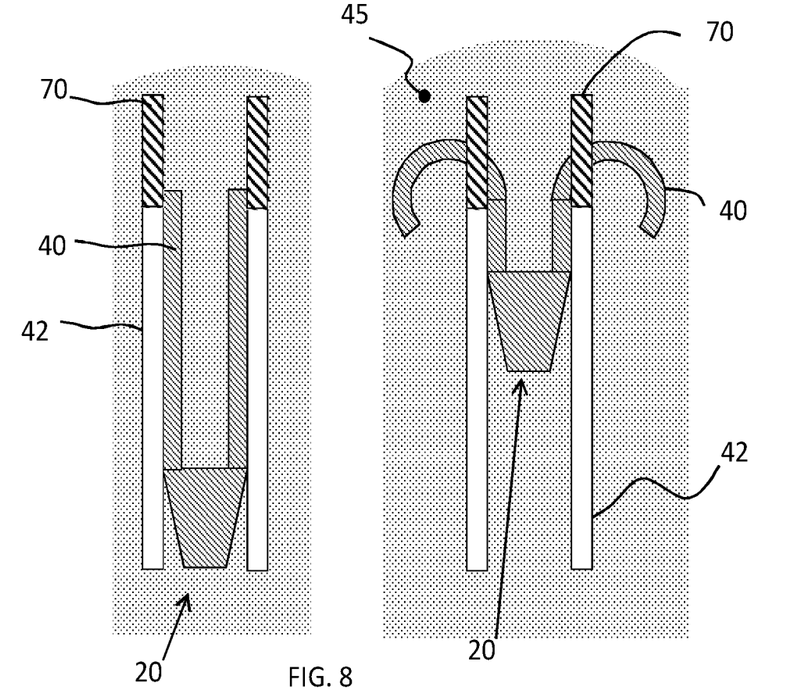
FIG. 8 shows a fourth example of tongue advancer system.
Figure 9:
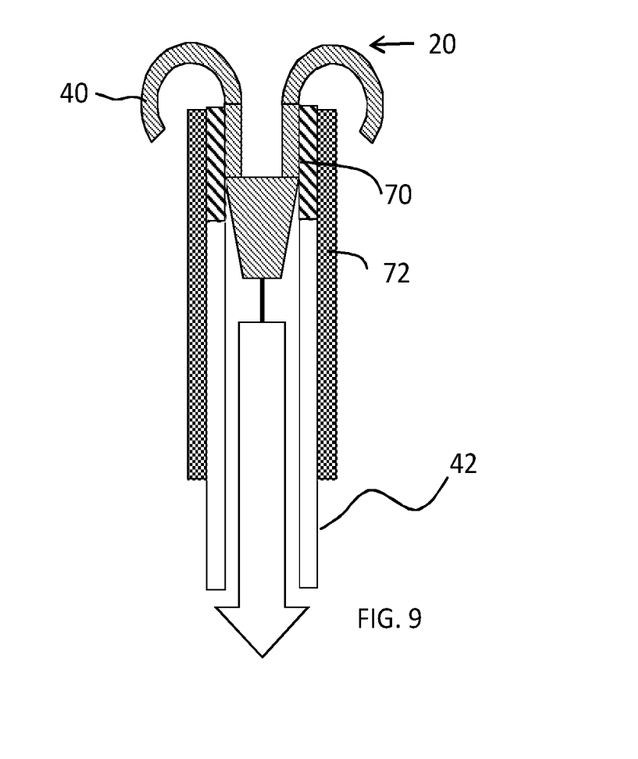
FIG. 9 is used to explain how the system of FIG. 8 is loaded into a delivery tube.
Figure 10:
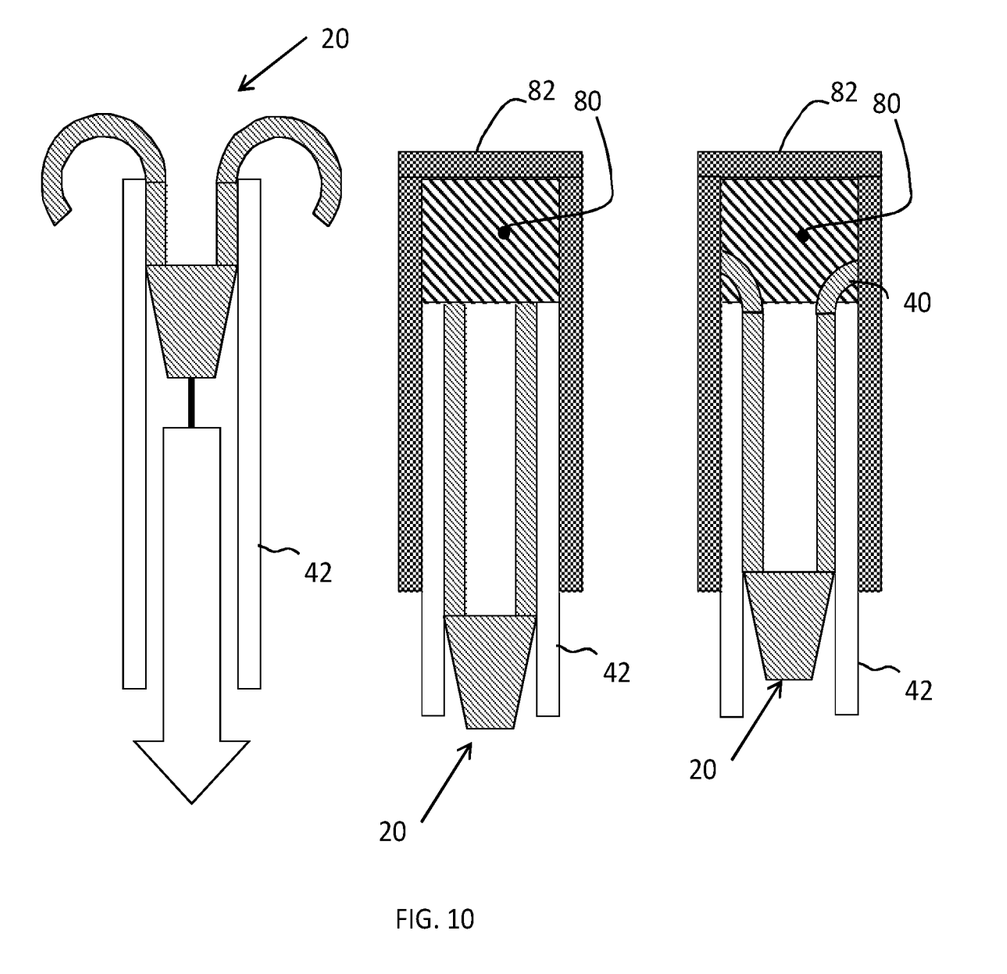
FIG. 10 shows a fifth example of tongue advancer system including a cap for loading.

FIGS. 8 to 10 relate to a second conceptual approach, in which the spacer provides an extension to the delivery tube.

As shown in the fourth example of FIG. 8, in the retracted configuration (left image), the fingers are straight and the spacer comprises an annular ring 70 around the forward ends of the fingers 40. In the deployed configuration (right image) the fingers 40 extend through the annular ring 70. During delivery of the tissue anchor, the fingers may either pierce the ring, or they may be aligned with suitable pre-formed lateral openings.

The system is simpler to align and manufacture without any lateral openings, by forming the spacer ring 70 from a material which can be punctured as mentioned above. The ring also should not deflect the fingers so that the natural expansion to a circular shape should not be compromised. The ring can be made from a soft material for this purpose.

Loading the tissue anchor into the delivery tube can no longer be carried out by just pulling the fingers straight into the delivery tube as the fingers will damage the soft ring extension. Thus, to load the tissue anchor 20 into the delivery tube 42, a further enclosing outer sleeve 72 can be used as shown in FIG. 9. An alternative is to mount the annular ring 70 after the tissue anchor has already been loaded into the delivery tube.

In this case, the spacer does not need to have a ring shape. It can instead be in the shape of a cap, as shown in the fifth example of FIG. 10.

The spacer comprises a cap 80 over the forward ends of the fingers in the retracted configuration.

The left image shows the tissue anchor 20 being loaded into the delivery tube 42.

The cap 80 is then mounted on top, and a casing 82 is used to hold the position of the cap correctly on top of the assembly, as shown in the middle image.

The tissue anchor 20 is then advanced slightly towards the deployed configuration. The deployment is carried out just enough let the tips of the fingers 40 penetrate the cap 80. In this way the cap is provisionally fixed as shown in the right image.

The casing 82 can then be removed and the total assembly including the cap can be inserted into the cannula.

An advantage of this approach is that the cap can be shaped freely as long as the outer diameter matches the cannula inner diameter. The cap can be rounded at the front circumference to facilitate insertion into the cannula. As the cap and delivery tube are not connected, the delivery tube can be retracted after delivery of the tissue anchor without any restriction. The cap then remains at the site of delivery in the tongue.

If withdrawal of the tissue anchor is needed, the cap can also be removed, by delicate loading of the deployed tissue anchor into the delivery/recapture tube. At the point that the fingers are sufficiently stretched but still projected into the cap both the tissue anchor and the cap can be pulled out. The same applies to the annular ring of FIGS. 8 and 9.

Thus, the examples according to this second conceptual approach also enable removal of the spacer, although with a more delicate procedure.

A third conceptual approach is to provide a spacer as a separate body, for example of a cylinder or ball shape that is inserted into the cannula first. This body will limit the insertion depth of the delivery tube carrying the tissue anchor. This separate spacer will not then easily be withdrawn.

The example of FIGS. 9 and 10 may be considered to provide the spacer as a modification to (and potentially a part of) the delivery tube (cannula). These examples thus provide a delivery tube which comprises a first section for insertion and removal from the tongue tissue. This is the main part of the delivery tube remote from the tongue. A second section is at the remote end which: i) functions as the spacer (70; 80) which extends beyond the maximum forward extent of the retractable fingers, or ii) is adapted to receive a spacer (70, 80) which extends beyond the maximum forward extent of the retractable fingers. The fingers are adapted to be able to pierce the spacer so that the spacer remains beyond the fingers. The same or similar mechanism as mentioned for positioning a spacer in a tissue anchor (snap-fit, screw threads, mechanism with audible and/or tactile feedback) may be used to position a spacer on a delivery tube.

The invention can be implemented as a small change to the known system. For this reason, full details of the known system have not been provided, such as the surgical equipment and procedure used to apply and configure the tongue manipulation device. The reader is directed to the prior literature, such as referenced above, for further details.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. An implantable tongue advancer system for use in a tongue manipulation device, comprising:
    a tissue anchor comprising a set of retractable fingers having a retracted configuration in which the tissue anchor is adapted to be loaded into a delivery tube and a deployed configuration in which the fingers are adapted for extending into tongue tissue in forward and lateral directions; and
    a spacer which extends from a first end positioned against a head of the tissue anchor to a second end beyond the maximum forward extent of the retractable fingers.

2. A tongue advancer system as claimed in claim 1, wherein in the retracted configuration, the fingers are straight and extend in an axial direction, wherein in a plane perpendicular to the axial direction, the fingers are arranged in a ring-shaped arrangement, and wherein the spacer comprises a shaft housed within the ring-shaped arrangement.

3. A tongue advancer system as claimed in claim 2, wherein the shaft is compressible in the axial direction.

4. A tongue advancer system as claimed in claim 3, wherein the shaft comprises a cylinder with slits along its length.

5. A tongue advancer system as claimed in claim 3, wherein the shaft is formed of an elastic material.

6. A tongue advancer system as claimed in claim 3, wherein the shaft comprises a base and a head with a non-rigid interconnection between the base and the head.

7. A tongue advancer system as claimed in claim 2, wherein the shaft extends from a back end of the fingers to a location which projects beyond the forward end of the fingers when the fingers are in their retracted configuration.

8. A tongue advancer system as claimed in claim 2, wherein the fingers in the deployed configuration have a loop radius, the shaft projects beyond the forward end by an amount (d) corresponding to the loop radius.

9. A tongue advancer system as claimed in claim 1, wherein in the retracted configuration, the fingers are straight and extend in an axial direction, wherein the spacer comprises an annular ring around the ends of the fingers in the retracted configuration.

10. A tongue advancer system as claimed in claim 9, wherein under reference to claim 9 the fingers extend through the annular ring in the extended configuration and the fingers extend through the cap in the extended configuration.

11. A tongue advancer system as claimed in claim 1, wherein in the retracted configuration, the fingers are straight and extend in an axial direction, wherein the spacer comprises a cap over the ends of the fingers in the retracted configuration.

12. A tongue advancer system as claimed in claim 1, wherein the spacer is biodegradable.

13. A tongue manipulation system, comprising a tongue advancer system as claimed in claim 1, a bone anchor for attachment to the mandible and
    a tether line which couples the tissue anchor of the tongue advancer system to the bone anchor.

14. A tissue anchor for use in an implantable tongue advancer system as claimed in claim 1, comprising:
    a set of retractable fingers having a retracted configuration in which the tissue anchor is adapted to be loaded into a delivery tube and a deployed configuration in which the fingers are adapted for extending into tongue tissue in forward and lateral directions; and
    a loading space between the fingers adapted to receive the spacer for extending beyond the maximum forward extent of the retractable fingers.

* * * * *